United States Patent
Brem et al.

(10) Patent No.: US 9,168,214 B2
(45) Date of Patent: Oct. 27, 2015

(54) METHODS OF INCREASING COLLAGEN FORMATION AND CELLULAR MIGRATION IN INTACT SKIN

(75) Inventors: Harold Brem, Bronx, NY (US); Marjana Tomic-Canic, Hillsdale, NJ (US)

(73) Assignee: New York University, New York, NY (US)

( * ) Notice: Subject to any disclaimer, the term of this patent is extended or adjusted under 35 U.S.C. 154(b) by 556 days.

(21) Appl. No.: 12/858,828

(22) Filed: Aug. 18, 2010

(65) Prior Publication Data

US 2010/0310517 A1 Dec. 9, 2010

Related U.S. Application Data

(63) Continuation of application No. 12/052,672, filed on Mar. 20, 2008, now abandoned.

(60) Provisional application No. 60/895,942, filed on Mar. 20, 2007.

(51) Int. Cl.
*A61K 38/18* (2006.01)
*A61K 8/64* (2006.01)
*A61Q 19/08* (2006.01)

(52) U.S. Cl.
CPC .............. *A61K 8/64* (2013.01); *A61K 38/1866* (2013.01); *A61Q 19/08* (2013.01); *C12N 2799/022* (2013.01); *C12N 2799/04* (2013.01)

(58) Field of Classification Search
None
See application file for complete search history.

(56) References Cited

U.S. PATENT DOCUMENTS

| | | | |
|---|---|---|---|
| 4,615,697 | A | 10/1986 | Robinson |
| 5,194,596 | A * | 3/1993 | Tischer et al. ............... 530/399 |
| 6,375,963 | B1 | 4/2002 | Repka |
| 6,821,524 | B2 | 11/2004 | Marini |
| 2003/0068297 | A1 | 4/2003 | Jain |
| 2003/0215412 | A1 | 11/2003 | Waugh |
| 2003/0235580 | A1 | 12/2003 | Zhang |
| 2004/0265268 | A1 | 12/2004 | Jain |

FOREIGN PATENT DOCUMENTS

| | | |
|---|---|---|
| EP | 1369107 | 12/2003 |
| JP | 2003081866 | 3/2003 |
| WO | 9013649 | 11/1990 |
| WO | 9404184 | 3/1994 |
| WO | 02098365 | 12/2002 |
| WO | 2006014089 | 2/2006 |

OTHER PUBLICATIONS

Detmar (J. Dermatological Sci. 24 Suppl: S78-S84, 2000).*
Xia et al. (Blood 102: 161-168, 2003).*
Larcher (Oncogene 17: 303-311, 1998).*
Kajiya et al. (Am. J.Pathol. 169(4): 1496-1503, 2006).*
Iriyama et al. (J. Invest. Dermatol. 126: No. Suppl. 1, pp. 2, 2006.*
Banks, et al., "Release of the angiogenic cytokine vascular endothelial growth factor (VEGF) from platelets: significance for VEGF measurements and cancer biology", Br J Cancer, 77:956-964 (1998).
Baumann, "Skin ageing and its treatment", J Pathol., 211(2):241-51 (2007).
Beer, et al., "Reduced expression of PDGF and PDGF receptors during impaired wound healing", J Invest Dermatol., 109: 132-138 (1997).
Berse, et al., "Vascular permeability factor (vascular endothelial growth factor) gene is expressed differentially in normal tissues, macrophages, and tumors", Mol Biol Cell, 3:211-220 (1992).
Bessman and Sapico, "Infections in the diabetic patient: the role of immune dysfunction andpathogen virulence factors", J Diabetes Complications, 4:258-262 (1992).
Brogi, et al., "Indirect angiogenic cytokines upregulate VEGF and bFGF gene expression in vascular smooth muscle cells, whereas hypoxia upregulates VEGF expression only", Circulation, 90:649-652 (1994).
Brown, et al., "PDGF and TGF-alpha act synergistically to improve wound healing in the genetically diabetic mouse", J Surg Research, 56:562-570 (1994).

(Continued)

*Primary Examiner* — Christine J Saoud
(74) *Attorney, Agent, or Firm* — Pabst Patent Group LLP

(57) ABSTRACT

It has been discovered that vascular endothelial growth factor ("VEGF") promotes migration of activated (but not differentiating) keratinocytes to skin. This growth factor specifically increases migration of keratinocytes of the "wounded skin" phenotype but does not have significant effects upon differentiated keratinocytes. It also increases collagen deposition and reduces wrinkles, enhances skin quality, and increases skin thickness to normal levels in individuals where skin has thinned due to age or disorder such as diabetes. It is particularly well suited for use as cosmeceuticals when applied in purified form and in known amounts. The data presented in the examples demonstrate efficacy and specificity of VEGF in enhancing migration of normal human keratinocytes as well as formation of new granulation tissue including collagen formation. VEGF induces keratinocyte and fibroblast migration, formation of new tissue, and not only induces deposition of collagen but improves alignment of the collagen fibers. Accordingly, this growth factor is highly suitable for use as a cosmeceutical, especially for skin resurfacing and reduction in wrinkles.

23 Claims, 1 Drawing Sheet

(56) References Cited

OTHER PUBLICATIONS

Connolly, et al., "Tumor vascular permeability factor stimulates endothelial cell growth and angiogenesis", J Clin Invest 84:1470-1478 (1989).
Darby, et al., "Apoptosis is increased in a model of diabetes-impaired wound healing in genetically diabetic mice", Int J Biochem Cell Biol, 29:191-200 (1997).
Dvorak, "Vascular permeability factor/vascular endothelial growth factor: a critical cytokine in tumor angiogenesis and a potential target for diagnosis and therapy", J Clin Oncol, 20:4368-4380 (2002).
Feige and van Eden, "Infection, autoimmunity and autoimmune disease", EXS., 77:359-373 (1996).
Ferrara, "Molecular and biological properties of vascular endothelial growth factor", J Mol Med, 77:524-543 (1999).
Fitzpatrick, et al., "Reversal of photodamage with topical growth factors: a pilot study", J. Cosmetic and Laser Therapy, 5(1):25-34 (2003).
Geerlings, et al., "Immune dysfunction in patients with diabetes mellitus (DM)", FEMS Immunol Med Microbial., 3-4:259-265 (1999).
Gospodarowicz, et al., "Isolation and characterization of a vascular endothelial cell mitogen produced by pituitary-derived folliculo stellate cells", PNAS, 86:7311-7315 (1989).
Greenhalgh, et al., "PDGF and FGF stimulate wound healing in the genetically diabetic mouse", Am J Pathol, 136:1235-1246 (1990).
Houck, et al., "The vascular endothelial growth factor family: identification of a fourth molecular species and characterization of alternative splicing of RNA", Mol Endocrin, 5:1806-1814 (1991).
Keck, et al., "Vascular permeability factor, an endothelial cell mitogen related to PDGF", Science, 246:1309-1312 (1989).
Koch, et al., "Interleukin-8 as a macrophage-derived mediator of angiogenesis", Science, 258:1798-1801 (1992).
Lauer, et al., "Expression and proteolysis of vascular endothelial growth factor is increased in chronic wounds", J Invest Derm, 115:12-18 (2000).
Leibovich and Ross, "The role of the macrophage in wound repair. A study with hydrocortisone and antimacrophage serum" Am J Pathol, 78:71-100 (1975).
Lerman et al., "Cellular dysfunction in the diabetic fibroblast: impairment in migration, vascular endothelial growth factor production, and response to hypoxia", Am. J. Pathol., 162:303-312 (2003).
Leung, et al., "Vascular endothelial growth factor is a secreted angiogenic mitogen", Science 246:1306-1309 (1989).
Li, et al., "Human recombinant vascular endothelial growth factor accelerates maturation of rat tail artery prefabricated flap", Surg Forum., 50:586-587 (1999).
Livant, et al., "The PHSRN sequence induces extracellular matrix invasion and accelerates wound healing in obese diabetic mice", J Clin Invest., 105:1537-1545 (2000).
Loots, et al., "Differences in cellular infiltrate and extracellular matrix of chronic diabetic and venous ulcers versus acute wounds", J Invest Dermatol., 5:850-857 (1998).
Matuxzewska, et al., "Acidic fibroblast growth factor: evaluation of topical formulations in a diabetic mouse wound healing model", Pharm Res, 11:65-71 (1994).
McColl, et al., "Plasmin activates the lymphangiogenic growth factors VEGF-C and VEGF-D", J Exp Med, 198:863-868 (2003).
Namiki, et al., "Hypoxia induces vascular endothelial growth factor in cultured human endothelial cells", J Biol Chem, 270:31189-31195 (1995).
Nathan, "Secretory products of macrophages", J Clin Invest, 79:319-326 (1987).
Neufeld, et al., "Vascular endothelial growth factor (VEGF) and its receptors", FASEB J., 13:9-22 (1999).
Nissen, et al., "Vascular endothelial growth factor mediates angiogenic activity during the proliferative phase of wound healing", Am J Path, 152:1445-1452 (1998).
Orringer, et al., "Tretinoin treatment before carbon-dioxide laser resurfacing: a clinical and biochemical analysis", J Am Acad Dermatol., 51(6):940-6 (2004).
Padubidri, et al., "Effect of vascular endothelial growth factor (VEGF) on survival of random extension of axial pattern skin flaps in the rat", Ann Plast Surg, 37:604-611 (1996).
Park, et al., "The vascular endothelial growth factor (VEGF) isoforms: differential deposition into the subepithelial extracellular matrix and bioactivity of extracellular matrix-bound VEGF", Mol Biol Cell, 4:1317-1326 (1993).
Senger, et al., "Purification and NH2-terminal amino acid sequence of guinea pig tumor-secreted vascular permeability factor", Cancer Res, 50:1774-1778 (1990).
Sorg, et al., "Proposed mechanisms of action for retinoid derivatives in the treatment of skin aging", J Cosmet Dermatol., 4(4):237-44 (2005).
Stavri, et al. "Basic fibroblast growth factor upregulates the expression of vascular endothelial growth factor in vascular smooth muscle cells. Synergistic interaction with hypoxia", Circulation, 92:11-14 (1995).
Sun, et al., "A new wound healing agent sphingosylphosphorylcholine", J Invest Dermatol., 106:232-237 (1996).
Sun, et al., "Transfection with aFGF cDNA improves wound healing", J Invest Dermatol, 108:313-318 (1997).
Tsuboi, et al., "Recombinant basic fibroblast growth factor stimulates wound healing in healing-impaired db/db mice", J Explorer Med, 172:245-251 (1990).
Uchida, et al., "Glomerular endothelial cells in culture express and secrete vascular endothelial growth factor", Am J Physiol, 266:F81-F88 (1994).
Wetzler, et al., "Large and sustained induction of chemokines during impaired wound healing in the genetically diabetic mouse: prolonged persistence of neutrophlis and macrophages during the late phase of repair", J Invest Dermatol., II5:245-253 (2000).
Witte, et al., "Nitric oxide enhances wound collagen deposition in diabetic rats", Surg Forum, 48:665-667 (1997).
Yamamota, et al., "Effect of topical application of a stable prostacyclin analogue, SM-10902 on wound healing in diabetic mice", Europ J Pharm, 302:53-60 (1996).
Yoshida, et al., "Differential endothelial migration and proliferation to basic fibroblast growth factor and vascular endothelial growth factor", Growth Factors, 13:57-64 (1996).
Zykova, et al., "Altered cytokine and nitric oxide secretion in vitro by macrophages from diabetic type II-like db/db mice", Diabetes, 49:1451-1458 (2000).

* cited by examiner

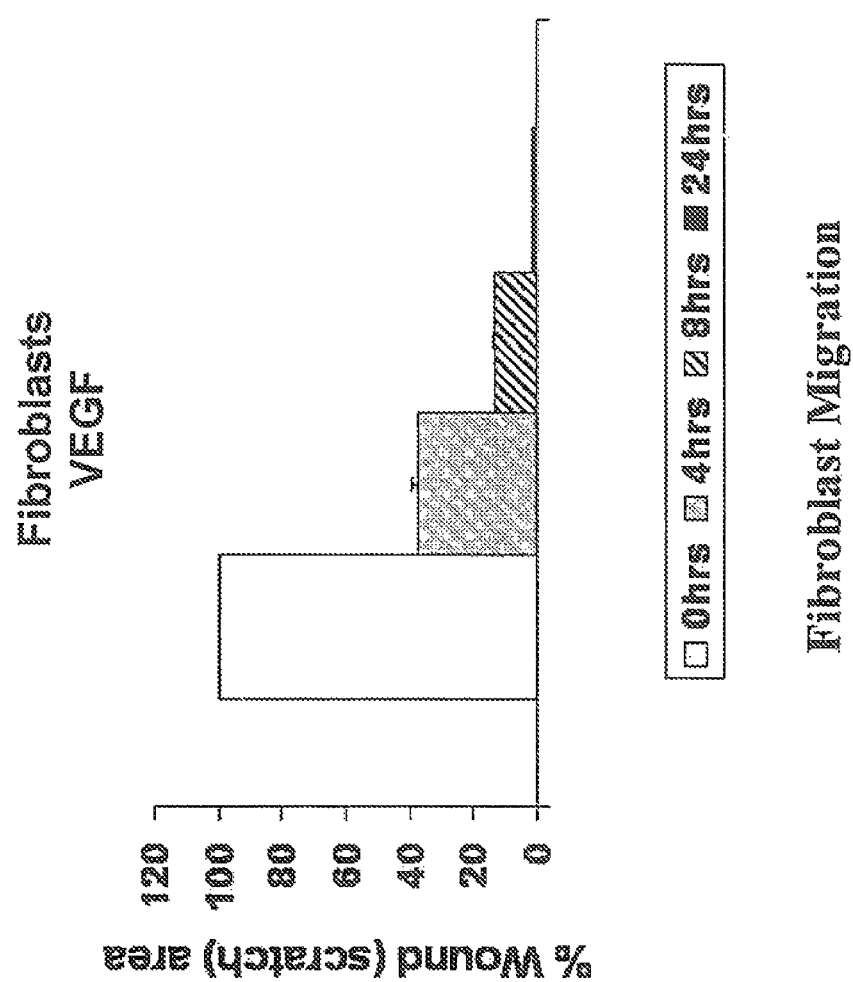

_US 9,168,214 B2_

METHODS OF INCREASING COLLAGEN FORMATION AND CELLULAR MIGRATION IN INTACT SKIN

CROSS-REFERENCE TO RELATED APPLICATIONS

This application is a continuation of pending prior application U.S. Ser. No. 12/052,672 filed Mar. 20, 2008, entitled "Growth Factor Mediated Cosmeceuticals and Use Thereof to Enhance Skin Quality", by Harold Brem and Marjana Tomic-Canic, and claims benefit of and priority to U.S. Provisional Application No. 60/895,942, filed Mar. 20, 2007, all of which are herein incorporated in their entirety by reference.

STATEMENT REGARDING FEDERALLY SPONSORED RESEARCH OR DEVELOPMENT

This invention was made with Government Support under Agreement DK059424 by the National Institutes of Health. The Government has certain rights in the invention.

FIELD OF THE INVENTION

The present invention is a cosmeceutical formulation containing VEGF, and methods of use thereof to improve skin quality, for example skin quality decreased by diabetes or aging.

BACKGROUND OF THE INVENTION

Current popular methods to treat facial signs of aging are many and very limited. The popular BOTOX® Cosmetic—with 3.3 million people receiving treatment last year—works by using a low dose of a potent toxin to temporarily paralyze the muscles surrounding the wrinkles, thus smoothing their appearance. However it is limited. Popular ingredients such as alpha-hydroxy acids and retinols can cause the skin to dry and tighten, which could worsen the appearance of wrinkles. Collagen injections can trigger allergic reactions or yield uneven results.

Vascular endothelial growth factor (VEGF), is known by most medical professionals as a sign for poor survival in cancer patients because a tumor will express higher levels of VEGF when it is metastasizing. VEGF serves an important function of facilitating new blood vessel formation. Therefore, a lot of medical attention has been paid to "anti-VEGF" components to try to inhibit the growth and spread of tumors. VEGF's ability to promote blood vessel formation is making it increasingly popular as an ingredient in various cosmeceutical products that claim to fight the appearance of aging skin. One of the biggest problems in treating wrinkles and other signs of aging is getting active ingredients past the natural protective barriers of the skin's surface. However, studies have shown that VEGF may serve to increase permeability in surfaces such as the skin, making its anti-aging effects even more potent.

One successful cosmetic application including VEGF is in Nouricel-MD®, manufactured by Advanced Tissue Sciences. U.S. Pat. No. 6,372,494 describes a method of obtaining growth factors in which cosmetic pursuits are stated as a possible use for the harvested growth factors. Nouricel-MD is used in a concentration of 93% by SkinMedica, a dermatological corporation, in their non-prescription product Tissue Nutrient Solution (TNS) Recovery Complex, which claims to "enhance skin texture, reduce the appearance of age spots and blotchiness, and improve skin elasticity". Its only claim specific to VEGF is that it is "believed to" stimulate blood vessel formation. The SkinMedica supports its claims by referencing one study, "Reversal of Photodamage with Topical Growth Factors: a Pilot Study" (Fitzpatrick, Rostan, 1995 Cosmetic Laser Associates).

The so-called "Transformation" line manufactured by Jan Marini Skin Research, Inc. contains a moisturizer, serum, and eye cream that all contain a mixture of growth factors, including VEGF. U.S. Pat. No. 6,821,524 details the use of VEGF as "it has been reported that VEGF increases the permeability of blood vessels" and uses a 1995 study by Palade and Roberts to support this claim. The Palade and Roberts study she cites, however, was not conducted on human skin, yet she claims in the parent "the compositions of the invention find use in improving the appearance of fine lines and wrinkles, i.e. in sun damaged skin, etc."

U.S. patent Application Nos. 20040265268 and 20030068297 both claim that a cosmetic product containing a blend of biological growth factors, including VEGF, would be effective to fight the appearance of aging skin, promote hair growth, as well as have wound-healing properties, based on its use as "a protein that stimulates the growth of new blood vessels". The applications claim that the products will "repair and rejuvenate mammalian skin" and "reduce the appearance of fine facial lines and wrinkles.

Aging skin is a common concern, and there is a large demand in the market for products to combat the appearance of aging skin, characterized by fine lines, wrinkles, age spots, and loss of elasticity. The latest for treatment of this aesthetic problem is the use of pharmaceutical components, like growth factors and retenoid in topical application. Such products are known unofficially as cosmeceuticals. These contain mixtures of many different things.

From a biological standpoint, an effective plan for rejuvenating and repairing skin must address the rejuvenation of skin cells at both the epidermal and the dermal layers, protection of the rejuvenated cells and cellular activity, stimulation of the production of skin matrix elements, and the sustainability of the rejuvenated conditions over the long term.

It is therefore an object to provide a purely biologic formulation that stimulates the dermis and epidermis and is dose responsive.

It is another object to provide compositions that enhance migration of keratinocytes and collagen deposition to reduce wrinkles, enhance skin quality, and increase skin thickness to normal levels in individuals where skin has thinned due to age or disorders such as diabetes, and which is useful as a cosmeceutical.

It is a further object of the present invention to provide a cosmeceutical containing controlled amounts of specific growth factors, which have defined dosage ranges and proven efficacy.

SUMMARY OF THE INVENTION

It has been discovered that vascular endothelial growth factor ("VEGF") promotes migration of activated (but not differentiating) keratinocytes to skin. This growth factor specifically increases migration of keratinocytes of the "wounded skin" phenotype but does not have significant effects upon differentiated keratinocytes. It also increases collagen deposition and reduces wrinkles, enhances skin quality, and increases skin thickness to normal levels in individuals where skin has thinned due to age or disorder such as diabetes. It is particularly well suited for use as cosmeceuticals when applied in purified form and in known amounts.

The data presented in the examples demonstrate efficacy and specificity of VEGF in enhancing migration of normal human keratinocytes as well as formation of new granulation tissue including collagen formation. VEGF induces keratinocyte and fibroblast migration, formation of new tissue, and not only induces deposition of collagen but improves alignment of the collagen fibers. Accordingly, this growth factor is highly suitable for use as a cosmeceutical, especially for skin resurfacing and reduction in wrinkles.

Formulations and methods of use thereof are described. A preferred formulation is a sustained release formulation, most preferably in an easy to administer topical formulation which enhances prolonged delivery and uptake of the growth factor to the skin, or a gene therapy vector. In a preferred embodiment, the carrier includes a pH buffering or neutralizing agent. The formulations may be applied topically to the skin, or adjacent to the site where increased keratinocyte and collagen deposition is desired, or injected or implanted within a sponge or other materials for use as a bulking agent which forms tissue in place of the implant. The formulation provides an effective amount of the growth factor over the necessary time to improve the skin quality, form new tissue, or enhance healing. It has been discovered that there is no additional beneficial effect with using a mixture of growth factors and such a combination may be detrimental. The effects of VEGF are not dependent on angiogenesis.

BRIEF DESCRIPTION OF THE DRAWINGS

FIG. 1 is a graph of the percent wound scratch area as a function of time (hours 0, 4, 8, and 24) demonstrating the rate of fibroblast migration.

DETAILED DESCRIPTION

Definitions

Activated keratinocytes are proliferating cells which have not exited the cell cycle (entered G0). Keratinocytes are "activated" during proliferative responses to injury and hyperproliferative disorders such as psoriasis and hyperplasias. Typically, differentiation or activation will be accompanied by expression of specific markers. The keratins K6 and K16 are two examples of markers expressed by "activated" keratinocytes. Differentiation is also usually marked by polarization of cells to have basal and apical polarity.

I. Formulations

VEGF

VEGF has been shown to be efficacious in the treatment of cardiac ischemia and leg ischemia, and it has demonstrated effectiveness in the treatment of diabetic limbs. The impaired wound healing in diabetics may be due to fibroblast dysfunction (Lerman et al. *Am. J. Pathol.*, 162:303-312 (2003)). Fibroblasts from diabetic db/db mice maintain selective impairments in multiple cellular processes which are accentuated by hypoxic environments such as those in a healing wound. These impairments include a severe reduction in VEGF expression, and release in response to injury. These changes were only observed after the development of the diabetic phenotype in these animals. VEGF levels are apparently decreased by endogenous proteases (Lauer, et al., *J Invest Derm*, 115:12-18 (2000)) in chronic wounds. The intense and sustained delivery of VEGF should obviate the proteolytic degradation of endogenous VEGF in the diabetic wound.

Prior to these studies, the primary role of VEGF has been thought to be in angiogenesis reflects its function as an endothelial cell mitogen, (Ferrara, *J Mol Med*, 77:524-543 (1999); Gospodarowicz, et al., *Proc Natl Acad Sci*, 86:7311-7315 (1989)) chemotactic agent, (Leung, et al., *Science* 246:1306-1309 (1989); Keck, et al., *Science* 246:1309-1312 (1989)) and inducer of vascular permeability (Connolly, et al., *J Clin Invest* 84:1470-1478 (1989); Yoshida, et al., *Growth Factors*, 13:57-64 (1996); Senger, et al., *Cancer Res*, 50:1774-1778 (1990)). Many of the cells (Banks, et al., *Br J Cancer*, 77:956-964 (1998), Nathan, *J Clin Invest*, 79:319-326 (1987); Berse, et al., *Mol Biol Cell*, 3:211-220 (1992); Leibovich, et al., *Am J Pathol*, 78:71-100 (1975); Koch, et al., *Science*, 258:1798-1801 (1993); Uchida, et al., *Am J Physiol*, 266:F81-F88 (1994); Namiki, et al., *J Biol Chem*, 270:31189-31195 (1995); Nissen, et al., *Am J Path*, 152:1445-1452 (1998); Brogi, et al., *Circulation*, 90:649-652 (1994); Stavri, et al. *Circulation*, 92:11-14 (1995)) recruited into a wound synthesize VEGF. VEGF serves distinct paracrine and autocrine roles upon endothelial cells. By stimulating the endothelial cells, multiple phases of the angiogenic cascade are enhanced by VEGF. VEGF has been shown in experimental studies to enhance vascularization of both autologous bone grafts and skin flaps in rats (Padubidri, et al., *Ann Plast Surg*, 37:604-611 (1996); Li, et al. *Surg Forum.*, 50:586-587 (1999)). One of the mediators of VEGF activity, nitric oxide, enhances collagen deposition in diabetic wounds, (Witte, et al., *Surg Forum*, 48:665-667 (1997)) and may restore endothelial function to improve both nerve conduction and tissue oxygenation. This supports the concept that VEGF enhances wound healing primarily by stimulating angiogenesis and possible secondary stimulation of collagen production.

Skin aging (intrinsic aging) and photoaging (extrinsic aging) involve a process that leads to the typical creased appearance of the skin, with the progressive loss of its physical and biologic properties. The loss of collagen is considered the characteristic histological finding in aged skin. Wrinkling and pigmentary changes are directly associated with photoageing and are considered its most salient cutaneous manifestations. Such photodamage represents the cutaneous signs of premature ageing. In addition, deleterious consequences of chronic sun exposure, specifically various forms of photo-induced skin cancer, are also linked to acute and chronic sun exposure. The only known strategies aimed at preventing photo-ageing include sun avoidance, using sunscreens to block or reduce skin exposure to UV radiation, using retinoids to inhibit collagenase synthesis and to promote collagen production, and using anti-oxidants, particularly in combination, to reduce and neutralize free radicals [Baumannn, *J Pathol.*, 211(2):241-51 (2007). Skin ageing and its treatment.]. Thus any bioactive agent that promotes proliferation of dermal fibroblasts, collagen production, collagen alignment as well as increase epidermal proliferation and increases blood flow will prevent and reverse signs of aging. In order to accomplish this using currently available compounds one would have to use combination of retinoids, BOTOX and additional fillers. VEGF alone accomplishes all of these effects, and therefore should be a very effective anti-aging molecule. In addition, the time in which one detects significant effects is much shorter (24 hrs to 2-3 weeks) compared to retinoids (6 months).

Studies demonstrate that VEGF has effects beyond angiogenesis and affects two key cells in skin: fibroblasts and keratinocytes—their migration, proliferation and other biological properties, such as collagen production, tensile strength etc. It has now been discovered, in contrast to previous studies that VEGF has a previously unknown activity in promoting migration of activated, but not differentiated, keratinocytes.

VEGF-A is a 45-kDa homodimeric glycoprotein with a diverse range of angiogenic activities. It exists in many isoforms with a common amino terminus that contains a signal sequence that allows the protein to be secreted. The VEGF-A gene consists of 8 exons and undergoes alternative splicing to yield mature isoforms of 121, 165, 189, and 206 amino acids (Houck, *Mol Endocrin*, 5:1806-1814 (1991)). In addition, some less commonly expressed variants have also been identified (VEGF$_{145}$ and VEGF$_{183}$) (Neufiled, et al., *FASEB J.*, 13:9-22 (1999)). VEGF$_{121}$ is freely secreted, whereas the largest isoforms (VEGF$_{189}$ and VEGF$_{206}$) are sequestered in the extracellular matrix (ECM) and require cleavage by proteases for their activation (Dvorak, *J Clin Oncol*, 20:4368-4380 (2002)). VEGF$_{165}$ exists in both a soluble and an ECM-bound form. The ECM-bound isoforms of VEGF-A, VEGF-C, and VEGF-D can be released in a diffusible form by plasmin cleavage at the C-terminus, which generates a bioactive fragment (Park, et al., *Mol Biol Cell*, 4:1317-1326 (1993); McColl, et al. *J Exp Med*, 198:863-868 (2003)). Alternatively, VEGF can be released from the ECM by MMP-9. VEGF$_{165}$ is the most common isoform and is preferred, although it is understood that other equivalent forms of VEGF are known and could be used alone or in combination with each other as described herein. Commercial Sources for VEGF include R&D Systems, Biosource, Apollo Cytokine Research and Millipore. It is understood that other equivalent forms of VEGF are known and could be used alone or in combination with each other as described herein.

B. Other Active Agents

Other therapeutic agents, for example, anti-microbial agents, pain relievers, anti-inflammatory agents, vitamins (e.g., vitamin B, C or E), aloe Vera or similar materials, may also be included. These typically enhance moisture retention or act by mechanisms other than through migration of keratinocytes or collagen deposition. VEGF can also be applied in combination with other skin treatments such as an exfolliant or laser treatment.

C. Carriers

1. Gene Therapy

The principle of gene therapy is that a therapeutic gene must first be efficiently delivered to the specific target cell (Nabel, et al., *Science*, 249:1285-1288 (1990)). Second, it must be expressed and sustained at a certain level to achieve its therapeutic purpose (Sauter, et al., *Proc Natl Acad Sci USA.*, 9:4802-4807 (2002)).

The replication-defective adenovirus vector is a safe and effective vehicle for gene delivery. Adenoviruses (ADV) are ideal gene therapy vectors because they infect a variety of both proliferating and quiescent human cell types, including skin cells, they remain episomal and do not integrate into the human genome. Moreover, they promote stable target gene expression in cells such as keratinocytes, melanocytes and fibroblasts for up to 6 weeks. ADV has been investigated as a gene delivery vector for a variety of therapeutic applications, including cancer, cardiovascular disease and congenital disease. Replication-deficient ADV strains have largely proven to be safe and effective.

After a tragic death in a gene replacement trial in which infusion of ADV vector directly into the hepatic artery resulted in fatal systemic inflammation and multi-system failure, subsequent clinical trials in cancer patients established a safe working dose range. Moreover, in recent studies localized ADV administration into sites such as tumors was well tolerated at effective doses without organ toxicity, elevation in serum proinflammatory cytokines or systemic dissemination of vector DNA in animals or people.

Localized VEGF gene therapy should increase treatment efficiency and avoid systemic side effects. Safe and effective gene-based delivery of VEGF requires efficient targeting to relevant cells, sustained expression at effective levels and localization without systemic absorption. Gene therapy has proven effective in a variety of experimental wound healing models, including on human fetal skin xenografts in SCID mice. ADV-mediated treatment of excisional skin wounds in these mice with platelet-derived growth factor (PDGF) produced an acute inflammatory response but this reaction did not impede wound healing, re-epithelialization, extracellular matrix deposition, granulation or wound closure. Human clinical trials with platelet-derived growth factor (PDGF) are currently underway.

The principle components of gene therapy are a vector or other means of delivering a nucleic acid of interest, and the nucleic acid. Many appropriate viral vectors are known, for example, adenoviral vectors, adeno-associated viral vectors or retroviral vectors. Other means of delivery include liposomes, direct delivery of naked DNA, and hydrogels. The vectors will typically include a promoter that can contain enhancers, inverted terminal repeats (ITRs), inducible promoters, and polyA sequences, followed by a termination sequence. All of these are known to those skilled in the art, and commercially available or described in the literature.

Suitable techniques for cloning, manipulation, modification and expression of nucleic acids, and purification of expressed proteins, are well known in the art and are described, for example, in Sambrook et al (2001) "Molecular Cloning, a Laboratory Manual", 3rd edition, Sambrook et al (eds), Cold Spring Harbor Laboratory Press, Cold Spring Harbor, N.Y., USA, incorporated herein by reference.

Growth factor encoding nucleic acids can be placed within linear or circular molecules. They can be placed within autonomously replicating molecules or within molecules without replication sequences. They can be regulated by their own or by other regulatory sequences, as is known in the art. Nucleic acid constructs encoding growth factor may include transcriptional regulatory elements, such as a promoter element, an enhancer or UAS element, and a transcriptional terminator signal, for controlling transcription of the growth factor sequences in the cells. Growth factor encoding nucleic acids can be used in expression cassettes or gene delivery vehicles, for the purpose of delivering a growth factor encoding mRNA, a full-length growth factor protein, a growth factor fusion protein, a growth factor encoding polypeptide, or a fragment of a growth factor encoding polypeptide, into a cell, preferably a eukaryotic cell. A gene delivery vehicle can be, for example, naked plasmid DNA, a viral expression vector, or a growth factor encoding nucleic acid in conjunction with a liposome or a condensing agent.

In one embodiment, the gene delivery vehicle comprises a promoter and a growth factor encoding nucleic acid. Examples of promoters that can be used include tissue-specific promoters and promoters that are activated by cellular proliferation, such as the thymidine kinase and thymidylate synthase promoters.

Other preferred promoters include promoters that are activated by infection with a virus, such as the a- and p-interferon promoters, and promoters that can be activated by a hormone, such as estrogen. Other promoters that can be used include the Moloney virus LTR, the CMV promoter, the mouse albumin promoter and adenovirus promoters.

A gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In some embodiments, the gene delivery vehicle is a recombinant retroviral vector. Recombinant retroviruses and various uses thereof have been described in numerous references including, for example, Mann, et al., *Cell*, 33:153-9 (1983), Cane and Mulligan, *Proc. Nat'l. Acad. Sci. USA*, 81:6349 (1984), Miller et al., *Human Gene Therapy*, 1:5-14 (1990), U.S. Pat. Nos. 4,405,712, 4,861,719, and 4,980,289, and PCT Application Nos. WO 89/002,468, WO 89/005,349, and WO 90/002,806. Numerous retroviral gene delivery vehicles can be utilized in the present invention, including for example those described in EP 0,415,731; WO 90/007936; WO 94/003622; WO 93/025698; WO 93/025234; U.S. Pat. No. 5,219,740; WO 93/011230; WO 93/010218; Vile and Hart, *Cancer Res.*, 53:3860-3864, (1993); Vile and Hart, *Cancer Res.*, 53:962-967 (1993); Ram et al., *Cancer Res.*, 53:83-88 (1993); Takamiya et al., *J. Neurosci. Res.*, 33:493-503 (1992); Baba et al., *J. Neurosurg.*, 79:729-735 (1993); (U.S. Pat. No. 4,777,127; GB 2,200,651; EP 0,345, 242 and WO91/102805).

Examples of retroviruses that can be utilized include avian leukosis virus (ATCC Nos. VR-535 and VR-247), bovine leukemia virus (VR-1313, murine leukemia virus (MLV), mink-cell focus-inducing virus (Koch, et al., *J Vir.*, 49:828 (1984) and Oliff, et al., *J Vir.*, 48:542-46 (1983)), murine sarcoma virus (ATCC Nos. VR-844,45010 and 45016), reticuloendotheliosis virus (ATCC Nos. VR-994, VR-770 and 4501 I), Rous sarcoma virus, Mason-Pfizer monkey virus, baboon endogenous virus, endogenous feline retrovirus (e.g., RD114), and mouse or rat gL30 sequences used as a retroviral vector. Strains of MLV from which recombinant retroviruses can be generated include 4070A and 1504A (Hartley and Rowe, J Vir., 19(1):19-25 (1976), Abelson (ATCC No. VR-999), Friend (ATCC No. VR-245), Graffi (Ru, et al., *J. Vir.*, 67:4722 (1993) and Yantchev, *Neoplasma*, 26:397, (1979)), Gross (ATCC No. VR-590), Kirsten (Albino, et al., *J. Exp. Med.*, 164:1710-22 (1986)), Harvey sarcoma virus (Manly, et al., *J. Vir.* 62:3540, 1988; and Albino et al., *J. Exp. Med.* 164: 1710, 1986) and Rauscher (ATCC No. VR-998), and Moloney MLV (ATCC No. VR-190). A nonmouse retrovirus that can be used is Rous sarcoma virus, for example, Bratislava (Manly, et al., *J Vir.* 62:3540-43 (1988) and Albino, et al., *J. Exp. Med.*, 164:1710-22 (1986)), Bryan high titer (e.g., ATCC Nos. VR-334, VR-657, VR-726, VR-659, and VR-728), Bryan standard (ATCC No. VR-140), Carr-Zilber (Adgighitov, et al., *Neoplasma*, 27:159, 1980), Engelbreth-Holm (Laurent, et al., *Biochem Biophys Acta*, 908:241 (1987), Harris, Prague (e.g., ATCC Nos. VR-772, and 45033), or Schmidt-Ruppin (e.g. ATCC Nos. VR-724, VR-725, VR-354) viruses.

Any of the above retroviruses can be readily utilized in order to assemble or construct retroviral gene delivery vehicles given the disclosure provided herein and standard recombinant techniques (e.g., Sambrook et al., Molecular Cloning: A Laboratory Manual, 2nd Edition (1989), Sambrook et al., Molecular Cloning: A Laboratory Manual, 3' d edition (2001), and Kunkle, *Proc. Natl. Acad. Sci. U.S.A.*, 82:488-92 (1985). Portions of retroviral expression vectors can be derived from different retroviruses. For example, retrovirus LTRs can be derived from a murine sarcoma virus, a tRNA binding site from a Rous sarcoma virus, a packaging signal from a murine leukemia virus, and an origin of second strand synthesis from an avian leukosis vims. These recombinant retroviral vectors can be used to generate transduction competent retroviral vector particles by introducing them into appropriate packaging cell lines (see Ser. No. 07/800,921, filed Nov. 29, 1991).

Recombinant retroviruses can be produced that direct the site-specific integration of the recombinant retroviral genome into specific regions of the host cell DNA. Such site-specific integration is useful for mutating or replacing the endogenous VEGF gene. Site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus. Packaging cell lines suitable for use with the above-described retroviral gene delivery vehicles can be readily prepared (see WO 92105266) and used to create producer cell lines (also termed vector cell lines or "VCLs") for production of recombinant viral particles. In some embodiments, packaging cell lines are made from human (e.g., HT1080 cells) or mink parent cell lines, thereby allowing production of recombinant retroviral gene delivery vehicles that are capable of surviving inactivation by human serum. The construction of such recombinant retroviral gene delivery vehicles is described in detail in WO 91102805. These recombinant retroviral gene delivery vehicles can be used to generate transduction competent retroviral particles by introducing them into appropriate packaging cell lines. Similarly, adenovirus gene delivery vehicles can also be readily prepared and utilized given the disclosure provided herein (see also Berkner, Biotechniques 6:616-627, 1988, and Rosenfeld, et al., *Science*, 252:431-434 (1991), WO 93/07283, WO 93/06223, and WO 93/07282).

A gene delivery vehicle can also be a recombinant adenoviral gene delivery vehicle. Such vehicles can be readily prepared and utilized given the disclosure provided herein and information available in the art (see, e.g., Berkner, *Biotechniques*, 6:616-29 (1988) and Rosenfeld, et al., *Science*, 252(5004):431-4 (1991), WO 93107283, WO 93106223, and WO 93107282). Adeno-associated viral gene delivery vehicles can also be constructed and used to deliver proteins or nucleic acids to cells in vitro or in vivo. The use of adeno-associated viral gene delivery vehicles in vitro is described in Chatteijee, et al., *Science*, 258:1485-1488 (1992), Walsh, et al., *Proc. Nat'l. Acad. Sci.*, 89:7257-7261 (1992), Walsh, et al., *J Clin. Invest.*, 94:1440-1448 (1994), Flotte, et al., *J. Biol. Chem.*, 268:3781-3790 (1993), Ponnazhagan, et al., *J. Exp. Med.*, 179:733-738 (1994), Miller, et al., *Proc. Nat'l Acad. Sci.*, 91:10183-10187 (1994), Einerhand, et al., *Gene Ther.*, 2:336-343 (1995), Luo, et al., *Exp. Hematol.*, 23:1261-1267 (1995), and Zhou, et al., *Gene Therapy*, 3.223-229 (1996). In vivo use of these vehicles is described in Flotte, et al., *Proc. Nat'l Acad. Sci*, 90:10613-10617 (1993), and Kaplitt, et al., *Nature Genet.*, 8:148-153 (1994).

In another embodiment, a gene delivery vehicle is derived from a togavirus. Such togaviruses include alphaviruses such as those described in WO 95/07994, WO 94/21792, and WO 92/10578. Several different alphavirus gene delivery vehicle systems can be constructed and used to deliver nucleic acids to a cell according to the present invention. Representative examples of such systems include those described in U.S. Pat. Nos. 5,091,309 and 5,217,879.

The recombinant viral vehicle can also be a recombinant alphavirus viral vehicle based on a Sindbis virus. Sindbis constructs, as well as numerous similar constructs, can be readily prepared. Sindbis viral gene delivery vehicles typically comprise a 5' sequence capable of initiating Sindbis virus transcription, a nucleotide sequence encoding Sindbis non-structural proteins, a viral junction region inactivated so as to prevent fragment transcription, and a Sindbis RNA polymerase recognition sequence. Optionally, the viral junction region can be modified so that nucleic acid transcription is reduced, increased, or maintained. As will be appreciated by those of ordinary skill in the art, corresponding regions from other alphaviruses can be used in place of those described above. The viral junction region of an alphavirus-derived gene delivery vehicle can comprise a first viral junction region that has been inactivated in order to prevent transcription of the nucleic acid and a second viral junction region that has been modified such that nucleic acid transcription is reduced. An alphavirus-derived vehicle can also include a 5' promoter capable of initiating synthesis of viral RNA from cDNA and a 3' sequence that controls transcription termination.

Other recombinant togaviral gene delivery vehicles that can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091, 309 and 5,217,879, as well as in WO 92/10578.

Other viral gene delivery vehicles include, for example, those derived from poliovirus (Evans, et al., *Nature,* 339:385 (1989) and Sabin, et al., *J. Biol. Standardization,* 1:1 15 (1973)) (ATCC VR-58); rhinovirus (Arnold, et al., *J. Cell. Biochem.*, L401 (1990)) (ATCC VR-1110); pox viruses, such as canary pox virus or vaccinia virus (Fisher-Hoch, et al., *Proc. Natl. Acad. Sci. U.S.A.,* 86:317-21 (1989); Flexner, et al., *Ann. N.Y. Acad. Sci.,* 569:86-103 (1989); Flexner, et al., *Vaccine,* 8:17-21 (1990); U.S. Pat. Nos. 4,603,112 and 4,769, 330; WO 89/01 973) (ATCC VR-111; ATCC VR-2010); SV40 (Mulligan, et al., *Nature,* 277:108-114 (1979)) (ATCC VR-305), (Madzak, et al., *J. Gen. Vir.,* 73: 1533-6 (1992)); influenza virus (Luytjes, et al., *Cell,* 59:1107-113 (1989); McMicheal et al., *The New England Journal of Medicine,* 309: 13-17 (1983); and Yap, et al., *Nature,* 273:238, 1978) (ATCC VR-797); parvovims such as adeno-associated virus (Samulski, et al., *J. Vir.,* 63:3822-8 (1989) and Mendelson, et al., *Virology,* 166:154-65 (1988)) (ATCC VR-645); herpes simplex virus (Kit, et al., *Adv. Exp. Med. Biol.,* 251:219-36 (1989)) (ATCC VR-977; ATCC VR-260); Mulligan, et al., *Nature,* 277: 108-114 (1979); human immunodeficiency virus (EPO 3 86,882; Buchschacher, et al., *J. Virol.,* 66:2731-9 (1992); measles virus (EPO 440,219) (ATCC VR-24); A (ATCC VR-67; ATCC VR-1247), Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre, et al., *Proc. Soc. Exp. Biol. Med.,* 121:190-3 (1966)) (ATCC VR-740).

Growth factor encoding nucleic acids can be introduced into the skin with agents that can facilitate uptake into cells of the skin using a variety of techniques that are available in the art. For example, a nucleic acid can be combined with a condensing agent to form a gene delivery vehicle. In some embodiments, the condensing agent is a polycation, such as polylysine, polyarginine, polyornithine, protamine, spermine, spermidine, and putrescine. Many suitable methods for making linkages between condensing agents and nucleic acids are known in the art.

Naked DNA is known to be taken up by muscle cells and transiently expressed in vivo, Wolff, et al., *Science,* 247:1465-1468 (1990); and Wolff, *Nature,* 352:815-818 (1991).

Plasmid DNA, which can function episomally, has been used with liposome encapsulation, Capo4 precipitation, and electroporation as an alternative to viral transfections. Clinical trials with liposome encapsulated DNA in treating melanoma illustrates this approach to gene therapy, as reported by Nabel, et al., *Proc. Nat. Acad. Sci. USA.,* 90:11307-11311 (1993) and Jiao, *Experimental Neurology,* 115:400-413 (1992) also reported expression of plasmid DNA. There have been many confirmatory reports since the initial studies.

In some embodiments, a growth factor encoding nucleic acid or polypeptide is associated with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell that has internalized the liposome, thereby releasing its contents into the cytoplasm. Prior to interaction with the surface of a cell, however, the liposome membrane acts as a relatively impermeable barrier that sequesters and protects its contents, for example, from degradative enzymes. Additionally, because a liposome is a synthetic structure, specially designed liposomes can be produced that incorporate desirable features. See, Stryer, Biochemistry, pp. 236-240, 1975 (W. H. Freeman, San Francisco, Calif.); Szoka, et al., *Biochim. Biophys. Acta,* 600:1-18 (1980); Bayer, et al., *Biochim. Biophys. Acta.* 550:464-73 (1979); Rivnay, et al., *Meth. Enzymol.* 149:119-123 (1987); Wang, et al., *Proc. Natl. Acad. Sci. U.S.A.* 84: 7851-5 (1987); Plant, et al., *Anal. Biochem.* 176: 420-6 (1989); and U.S. Pat. No. 4,762,915.

Liposomes can encapsulate a variety of nucleic acid and polypeptide molecules including DNA, RNA, plasmids, expression constructs comprising nucleic acids such those disclosed herein, and VEGF polypeptides. Liposomal preparations include cationic (positively charged), anionic (negatively charged) and neutral preparations. Cationic liposomes have been shown to mediate intracellular delivery of plasmid DNA (Feigner, et al., *Proc. Natl. Acad. Sci. USA,* 84:7413-7416 (1987)), mRNA (Malone, et al., *Proc. Natl. Acad. Sci. USA,* 86:6077-6081 (1989)), and purified transcription factors (Debs, et al, *J. Biol. Chem.,* 265:10189-10192 (1990), in functional form. Cationic liposomes are readily available. For example, N[1-2,3-dioleyloxy)propyl]-N,N,N-triethylammonium (DOTMA) liposomes are available under the trademark Lipofectin™, (GIBCO BRL, Grand Island, N.Y.), Transfectace (DDAB/DOPE) and DOTAP/DOPE (Boerhinger). Other cationic liposomes can be prepared from readily available materials using techniques available in the art. See, e.g., Szoka, et al., *Proc. Natl. Acad. Sci. USA,* 75:4194-4198 (1978); and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE)e. These materials can also be mixed with the DOTMA and DOTAP starting materials in appropriate ratios. Methods for making liposomes using these materials are well known in the art.

The liposomes can comprise multilamellar vesicles (MLVs), small unilamellar vesicles (SUVs), or large unilamellar vesicles (LUVs). The various liposome-nucleic acid complexes are prepared using methods known in the art. See, e.g., Straubinger, et al., *Methods of Immunology*, 101:512-527 (1983); Szoka, et al., *Proc. Natl. Acad. Sci. USA*, 87:3410-3414 (1990); Papahadjopoulos, et al., *Biochim. Biophys. Acta*, 394:483-91 (1975); Wilson, et al., *Cell*, 17:77-84 (1979); Deamer and Bangham, *Biochim. Biophys. Acta*, 443:629-34 (1976); Ostro, et al., *Biochem. Biophys. Res. Commun.*, 76:836-42 (1977); Fraley, et al., *Proc. Natl. Acad Sci. USA*, 76:3348-52 (1979); Enoch and Strittmatter, *Proc. Natl. Acad Sci. USA*, 76: 145-9 (1979); Fraley, et al., *J. Biol. Chem.*, 255:10431-5 (1980) and Schaefer-Ridder, et al., *Science*, 215:166-8 (1982).

In addition, lipoproteins can be included with a nucleic acid for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of nucleic acids to cells expressing lipoprotein receptors. In some embodiments, if lipoproteins are included with a nucleic acid, no other targeting ligand is included in the composition. Receptor-mediated targeted delivery of VEGF nucleic acids to specific tissues can also be used.

Receptor-mediated DNA delivery techniques are described in, for example, Findeis, et al., *Trends in Biotechnol.* 11:202-05 (1993); Chiou, et al. (1994), Gene Therapeutics: Methods and Applications of Direct Gene Transfer (J. A. Wolff, ed.); Wu & Wu, *J Biol. Chem.* 263:621-24 (1988); Wu, et al., *J. Biol. Chem.*, 269:542-46 (1994); Zenke, et al., *Proc. Natl. Acad. Sci. USA*, 87:3655-59 (1990); Wu, et al., *J. Biol. Chem.*, 266:338-42 (1991.

In another embodiment, naked nucleic acid molecules are used as gene delivery vehicles, for example, as described in WO 9011 1092 and U.S. Pat. No. 5,580,859. Such gene delivery vehicles can be either DNA or RNA and, in certain embodiments, are linked to killed adenovirus. Curiel, et al., *Hum. Gene. Ther.*, 3:147-154 (1992). Other suitable vehicles include DNA-ligand (Wu, et al., *J. Biol. Chem.* 264:16985-16987 (1989)), lipid-DNA combinations (Feigner, et al., *Proc. Natl. Acad. Sci. USA*, 84:7413 7417 (1989)), liposomes (Wang, et al., *Proc. Natl. Acad. Sci. USA.*, 84:7851-7855 (1987)) and microprojectiles (Williams, et al., *Proc. Natl. Acad. Sci. USA.*, 88:2726-2730 (1991)).

One can increase the efficiency of naked nucleic acid uptake into cells by coating the nucleic acids onto biodegradable latex beads. This approach takes advantage of the observation that latex beads, when incubated with cells in culture, are efficiently transported and concentrated in the perinuclear region of the cells. The beads will then be transported into cells when injected into muscle. Nucleic acid-coated latex beads will be efficiently transported into cells after endocytosis is initiated by the latex beads and thus increase gene transfer and expression efficiency. This method can be improved further by treating the beads to increase their hydrophobicity, thereby facilitating the disruption of the endosome and release of nucleic acids into the cytoplasm.

Growth factor-encoding nucleic acids can be introduced into cells using mehanical methods, such as microinjection, liposome-mediated transfection, electroporation, or calcium phosphate precipitation. Alternatively, if it is desired that the cells stably retain the DNA construct, the DNA construct can be supplied on a plasmid and maintained as a separate element or integrated into the genome of the cells, as is known in the art.

Expression of an endogenous growth factor encoding gene in a cell can also be altered by introducing in frame with the endogenous growth factor encoding gene a DNA construct comprising a growth factor targeting sequence, a regulatory sequence, an exon, and an unpaired splice donor site by homologous recombination, such that a homologous recombinant cell comprising the DNA construct is formed. The new transcription unit can be used to turn the growth factor encoding gene on or off as desired. This method of affecting endogenous gene expression is taught in U.S. Pat. No. 5,641,670.

Integration of a delivered growth factor encoding nucleic acid into the genome of a cell line or tissue can be monitored by any means known in the art. For example, Southern blotting of the delivered growth factor encoding nucleic acid can be performed. A change in the size of the fragments of a delivered nucleic acid indicates integration. Replication of a delivered nucleic acid can be monitored inter alia by detecting incorporation of labeled nucleotides combined with hybridization to a growth factor encoding probe. Expression of a growth factor encoding nucleic acid can be monitored by detecting production of growth factor encoding mRNA that hybridizes to growth factor encoding nucleic acid or by detecting growth factor protein. Growth factor protein can be detected immunologically.

In general the viral vectors preferred for gene therapy include human adenoviruses having a 36-kilobase double-stranded DNA genome that undergoes a highly regulated program of gene expression during the normal life cycle of the virus. The advantages of adenoviruses over other chemical, physical, or biological gene transfer techniques include several unique features of this system (Molnar-Kimber, et al., *Hum Gene Ther*, 9(14):2121-33 (1998)). First, adenoviruses infect human skin cells at more than 95% efficiency and do not require that cells are dividing, making a lengthy selection process unnecessary (Kozarsky, et al., *Curr Opin Genet Dev,* 3(3):499-503 (1993); Mulligan, *Science*, 260(5110):926-32 (1993); Kremer, *Gene Ther.*, 2:564-5 (1995); Yang, et al., *Immunity*, 1(5):433-42 (1994); Mitani, et al., *Proc Natl Acad Sci USA*, 92(9):3854-8 (1995)). Second, adenoviruses remain episomal and thus do not normally integrate into the human genome (Bett, et al., *J Viral.*, 67(10):5911-21 (1993) and Losordo, et al., *Am Heart J*, 138:132-141 (1999)). Third, adenovirus-mediated gene expression in keratinocytes, melanocytes, and fibroblasts remains stable in vitro for at least 2-6 weeks, depending on the proliferation rate of cells (Feng, et al., *Cancer Res.*, 55(10):2024-8 (1995)). Adenoviral vectors are commonly constructed by deletion of the essential ELAM-1 gene to prevent viral replication.

2. Topical Carriers

The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated (intradermally or subcutaneously). The active compositions can also be delivered via iontophoresis, e.g., as disclosed in U.S. Pat. No. 4,140,122; 4,383,529; or 4,051,842.

The cosmecutical formulations may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents include water and physiologically acceptable buffered saline solutions such as phosphate buffered saline solutions with a substantially neutral pH. Additives may be mixed in with the formulation for maximum or desired efficacy of the delivery system or for the comfort of the patient. Such additives include, for example, lubricants, plasticizing agents, preservatives, gel formers, film formers, cream formers, disintegrating agents, coatings, binders, vehicles, coloring agents, odor controlling agents, humectants, viscosity controlling agents, pH-adjusting agents, and similar agents.

In a preferred embodiment, the compositions contain sufficient amounts of at least one pH buffering agent to ensure that the composition has a final pH of about 3 to about 11, preferably between 6 and 8, most preferably at or near the pH of the skin. Suitable pH modifying agents include, but are not limited to, sodium hydroxide, citric acid, hydrochloric acid, acetic acid, phosphoric acid, succinic acid, sodium hydroxide, potassium hydroxide, ammonium hydroxide, magnesium oxide, calcium carbonate, magnesium carbonate, magnesium aluminum silicates, hydroxyapatite, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

The percent by weight of the active agents present in a formulation will depend on various factors, but generally will be from about 0.01% to about 98% of the total weight of the formulation, and typically about 0.1 to about 90% by weight, more typically less than 50%, most typically in the range of 0.5 to 10%. Reference is also made to the following examples which demonstrate the dose response curves for the formulations applied to appropriate animal models.

Emulsions, Ointments and Creams

The cosmeceutical compositions can be formulated as emulsions for topical application. An emulsion contains one liquid distributed the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol.

The oil phase may contain other oily pharmaceutically approved excipients. For example, materials such as hydroxylated castor oil or sesame oil may be used in the oil phase as surfactants or emulsifiers.

Suitable surfactants include, but are not limited to, anionic surfactants, non-ionic surfactants, cationic surfactants, and amphoteric surfactants. Examples of anionic surfactants include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinnate, disodium lauryl sulfosuccinate, diammonium lauryl sulfosuccinate, tetrasodium N-(1,2-dicarboxyethyl)-N-octadecylsulf-osuccinnate, diamyl ester of sodium sulfosuccinic acid, dihexyl ester of sodium sulfosuccinic acid, dioctyl esters of sodium sulfosuccinic acid, docusate sodium, and combinations thereof.

Examples of nonionic surfactants include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethyelen oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Examples of amphoteric surfactants include, but are not limited to, sodium N-dodecyl-γ-alanine, sodium N-lauryl-γ-iminodipropionate, myristoamphoacetate, lauryl betaine, lauryl sulfobetaine, sodium 3-dodecyl-aminopropionate, sodium 3-dodecylaminopropane sulfonate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, oleamidopropyl betaine, cow dimethyl sulfopropyl betaine, stearyl dimethyl sulfopropyl betaine, lauryl dimethyl sulfoethyl betaine, lauryl bis-(2-hydroxyethyl)sulfopropyl betaine, and combinations thereof.

Examples of cationic surfactants include, but are not limited to, behenyl trimethyl ammonium chloride, bis(acyloxyethyl)hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowedimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, lautrimonium chloride, methyl-1-oleyl amide ethyl-2-oleyl imidazolinium methyl sulfate, picolin benzyl ammonium chloride, polyquaternium, stearalkonium chloride, sterayl dimethylbenzyl ammonium chloride, stearyl trimethyl ammonium chloride, trimethylglycine, and combinations thereof.

Suitable suspending agents include, but are not limited to, alginic acid, bentonite, carbomer, carboxymethylcellulose and salts thereof, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable antioxidants include, but are not limited to, butylated hydroxytoluene, alpha tocopherol, ascorbic acid, fumaric acid, malic acid, butylated hydroxyanisole, propyl gallate, sodium ascorbate, sodium metabisulfite, ascorbyl palmitate, ascorbyl acetate, ascorbyl phosphate, Vitamin A, folic acid, flavons or flavonoids, histidine, glycine, tyrosine, tryptophan, carotenoids, carotenes, alpha-Carotene, beta-Carotene, uric acid, pharmaceutically acceptable salts thereof, derivatives thereof, and combinations thereof.

Suitable chelating agents include, but are not limited to, EDTA, disodium edetate, trans-1,2-diaminocyclohexane-N,N,N',N'-tetraaceticacid monohydrate, N,N-bis(2-hydroxyethyl)glycine, 1,3-diamino-2-hydroxypropane-N,N,N',N'-tetraacetic acid, 1,3-diaminopropane-N,N,N',N'-tetraacetic acid, ethylenediamine-N,N'-diacetic acid, ethylenediamine-N,N'-dipropionic acid, ethylenediamine-N,N'-bis(methylenephosphonic acid), N-(2-hydroxyethypethylenediamine-N,N,N'-triacetic acid, ethylenediamine-N,N,N,N-tetrakis (methylenephosphonic acid), O,O'-bis(2-aminoethyl) ethyleneglycol-N,N,N',N'-tetraacetic acid, N,N-bis(2-hydroxybenzyl)ethylenediamine-N,N-diacetic acid, 1,6-hexamethylenediamine-N,N,N',N'-tetraacetic acid, N-(2-hydroxyethyl)iminodiacetic acid, iminodiacetic acid, 1,2-diaminopropane-N,N,N',N'-tetraacetic acid, nitrilotriacetic acid, nitrilotripropionic acid, nitrilotris(methylenephosphoric acid), 7,19,30-trioxa-1,4,10,13,16,22,27,33-octaazabicyclo[11,11,11]pentatriacontane hexahydrobromide, triethylenetetramine-N,N,N',N'',N''',N''''-hexaacetic acid, and combinations thereof.

Suitable emollients include, but are not limited to, myristyl lactate, isopropyl palmitate, light liquid paraffin, cetearyl alcohol, lanolin, lanolin derivatives, mineral oil, petrolatum, cetyl esters wax, cholesterol, glycerol, glycerol monostearate, isopropyl myristate, lecithin, and combinations thereof thereof.

Suitable humectants include, but are not limited to, glycerin, butylene glycol, propylene glycol, sorbitol, triacetin, and combinations thereof.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. Oil-In-Water emulsions can also be utilized in the compositions, patches, bandages and articles. These systems are semisolid emulsions, micro-emulsions, or foam emulsion systems. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants.

Inserts

In some embodiments, the active ingredients can be formulated with oleaginous bases or ointments to form a semisolid composition with a desired shape. For example, the composition can be shaped for easy application to, or insertion into, a wound, ulcer, puncture wound or surgical site. This class of formulations comprises the active ingredients and hydrocarbon-based semisolids. In addition to the active ingredients, these semisolid compositions can contain dissolved and/or suspended bactericidal agents, preservatives and/or a buffer system. The petrolatum component in these bases can be any paraffin ranging in viscosity from mineral oil employing incorporated isobutylene, colloidal silica, or stearate salts to paraffin waxes. White and yellow petrolatums are examples of such systems. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to 1.06 centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl(lower)alkyl, such as benzyl. In such a moiety, each lower alkyl or alkenyl group preferably has 1 to 3 carbons inclusive, such as in a dimethylsiloxane polymer.

Absorption bases can be used with such an oleaginous system. In addition to the active ingredients, additional ingredients with the capacity to emulsify a significant quantity of water are employed. Water-in-oil (w\o) emulsions can be formed wherein the external phase is oleaginous in character.

Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobellipophobe balance) emulsifiers, and assorted ionic and nonionic surfactants, singularly or in combination.

Controlled Release Formulations

Controlled or sustained release can be achieved by the addition of time-release additives, such as polymeric structures, matrices, that are available in the art. For example, the compositions may also be administered through the use of hot-melt extrusion articles, such as bioadhesive hot-melt extruded film (see, for example, U.S. Pat. No. 6,375,963). The formulation can comprise a cross-linked polycarboxylic acid polymer formulation, generally described in U.S. Pat. No. 4,615,697. In general, about eighty percent of the monomers of the polymer in such a formulation contain at least one carboxyl functionality. The cross-linking agent should be present at such an amount as to provide enough adhesion to allow the system to remain attached to the target epithelial or endothelial cell surfaces for a sufficient time to allow the desired release to take place.

An insert, transdermal patch, bandage or article can comprise a mixture or coating of polymers that provide release of the active agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients. Such a water-soluble pore-forming agent can be polyethylene glycol, polypropylene glycol, a mixture or polymer of sugars (lactose, sucrose, dextrose, etc.), salts, poloxamers, hydroxypropylcellulose, polyvinyl alcohol and other water-soluble food grade and other excipients.

The inserts, articles, transdermal patches and bandages may also comprise a water insoluble polymer. Examples of such polymers are ethylcellulose, acrylic resins, co-polymer of methacrylic acid and acrylic acid ethyl ester, polylactic acid, PLGA, polyurethane, polyethylene vinyl acetate copolymer, polystyrene-butadiene copolymer and silicone rubber, or mixtures thereof. For example, polymers sold under trade names Aquacoat ECD 30 and Eudragit RS 30 and NE 30D (registered trademarks of Rhom Tech, Inc.) can be used. These are particularly suitable for administration to sites where pH change can be used to effect release. These rate controlling polymers can be applied using a continuous coating film during the process of spraying and drying with active agents. The rate controlling film prepared with such a polymer is stable during implantation. The film should have enough strength to withstand tear and inner osmotic pressure, and have the stability not to swell or hydrate during the implantation life. In one embodiment, the coating formulation is used to coat pellets comprising the active ingredients that are compressed to form a solid, biodegradable insert.

A polymer formulation can also be utilized to provide controlled or sustained release. Such a polymer formulation can be adjusted to control the release rate of the hyaluronic acid by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene and similar agents. One example of a polymer for use in such a formulation is Polycarbophil, U.S.P., which is commercially available from B. F. Goodrich Specialty Polymers of Cleveland, Ohio under the trade name NOVEON™-AAL The United States Pharmacopeia, 1995 edition, United States Pharmacopeial Convention, Inc., Rockville, Md., at pages 1240-41, indicates that polycarbophil is a polyacrylic acid, cross-linked with divinyl glycol.

Other useful bioadhesive polymers that may be used in such a delivery system formulation are mentioned in U.S. Pat. No. 4,615,697. Typically, these polymers would not be used in their salt form, because this would decrease their bioadhesive capability. Such bioadhesive polymers may be prepared by conventional free radical polymerization techniques utilizing initiators such as benzoyl peroxide, azobisisobutyronitrile. Exemplary preparations of useful bioadhesives are provided in U.S. Pat. No. 4,615,697. As will be apparent to those skilled in the art, the composition can be varied to affect certain properties of the formulation. For example, the viscosity can be varied by varying the concentration of therapeutic agents and carriers, or by adding a polymer or gel former.

Alternatively, the growth factor is delivered using a sustained release device. Both non-biodegradable and biodegradable matrices can be used for delivery of genes, although biodegradable matrices are preferred. These may be natural or synthetic polymers, although synthetic polymers are preferred due to the better characterization of degradation and release profiles. The polymer is selected based on the period over which release is desired, generally in the range of at least two to six weeks, although longer periods may be desirable. In some cases linear release may be most useful, although in others a pulse release or "bulk release" may provide more effective results. The polymer may be in the form of a hydrogel (typically absorbing up to about 90% by weight of water), and can optionally be crosslinked with multivalent ions or polymers.

High molecular weight genes can be delivered partially by diffusion but mainly by degradation of the polymeric system. In this case, biodegradable polymers, bioerodible hydrogels, and protein delivery systems are particularly preferred. Examples of non-biodegradable polymers include ethylene vinyl acetate, poly(meth)acrylic acid, polyamides, copolymers and mixtures thereof. Examples of biodegradable polymers include synthetic polymers such as hydroxyacid polymers, for example, polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In one embodiment, the polymeric matrix is a microparticle between nanometers and one millimeter in diameter, more preferably between 0.5 and 100 microns for administration via injection. The microparticles can be microspheres, where the gene is dispersed within a solid polymeric matrix, or microcapsules, where the core is of a different material than the polymeric shell, and the gene is dispersed or suspended in the core, which may be liquid or solid in nature. Unless specifically defined herein, microparticles, microspheres, and microcapsules are used interchangeably.

Alternatively, the polymer may be cast as a thin slab or film, ranging from nanometers to four centimeters, a powder produced by grinding or other standard techniques, or even a gel such as a hydrogel. The polymer can also be in the form of a coating or part of a bandage, stent, catheter, vascular graft, or other prosthetic device.

The matrices can be formed by solvent evaporation, spray drying, solvent extraction and other methods known to those skilled in the art.

The release of growth factor from fibrin-based biomaterials was demonstrated by Wong, et al., *Thromb Haemost.*, 89(3):573-82 (2003). Fibrin-based biomaterial preparations can be used as provisional growth matrices for cells important in tissue repair during wound healing in vivo. Growth factor was incorporated into the fibrin biomaterials prior to formation of the Fibrin Sealant clots. Clotting resulted in sustained release of growth factor causing angiogenic activity.

One embodiment provides a sustained-release gel. The gel is made of a pharmaceutical composition including a soluble, gelable peptide salt and up to 30 percent, by weight, of a pharmaceutically acceptable, soluble carrier, and one or more bodily fluids of the patient, wherein the peptide salt automatically forms the gel after interaction with the bodily fluids, and the gel releases the peptide continuously within the patient over a period of at least three days after formation. The pharmaceutical composition that forms the gel can be a solid, or it can further include a solvent, e.g., sterilized water, in an amount less than 50 percent of the amount of solvent required to dissolve the peptide salt and to provide the pharmaceutical composition with a semisolid consistency.

Another embodiment provides a growth factor peptide incorporated in a conventional hydrophobic polymer matrix, e.g. of a polylactide, which is made more accessible for water by introducing a hydrophilic unit, e.g. of polyethyleneglycol, polyvinylalcohol, dextran or polymethacrylamide. The hydrophilic contribution to the amphipathic polymer is given by all the ethylene oxide groups in case of a polyethylene glycol unit, by the free hydroxyl groups in the case of a polyvinylalcohol unit or of a dextran unit, and by the amide groups in the case of a polymethyacrylamide unit.

Many sustained release formulations for delivery of peptides are known. See, for example, U.S. Pat. Nos. 5,595,760; 5,538,739, 5,876,761, 5,639,480, 5,688,530, 6,534,094, 7,109,166, 6,777,386, 6,337,318, and 6,528,093.

Kits and Devices

The formulations may be provided as a packaged cosmeceutical, such as a kit or other container. The kit or container holds an effective amount of VEGF for promoting keratinocyte migration, fibroblast proliferation, collagen production, proper collagen alignment, macrophage infiltration in the skin, and increasing subdermal fat and instructions for using the pharmaceutical composition for repairing or regenerating skin. The pharmaceutical composition includes a composition, in an effective amount as defined herein. In some embodiments the composition is provided as part of a bandage. For example, the compositions can be applied to one side of a bandage or a transdermal patch, or the bandage or patch can be saturated with a liquid suspension of the composition.

Liquid compositions can be administered from absorbent materials, such as a bandage, patch or sponge, or as a spray or aerosol (applied to the affected area using a pump-type or aerosol sprayer). The use of a patch or bandage, into which the composition has been incorporated, is advantageous in that it the composition will be slowly and continuously released. Providing the composition in the form of a solution, which may initially be provided in a concentrated liquid form, or as a sterile dissolvable powder, for example, in a packet or syringe, requiring the addition of water, saline or other suitable diluents prior to use may be advantageous.

Solid compositions can be applied by any number of means, including the use of applicators or by patient self-administration. For example, creams, lotions, foams, pastes, ointments, or gels may be administered using an applicator, such as a squeeze-type or plunger-type applicator. Administering the composition as a suppository is advantageous as it provides convenience, ease of application, increased safety and/or neatness. Administering the composition as a cream having low surface tension is advantageous as it provides a uniform wetting action that assists in composition penetration into crypts and crevices of the wound. Such a creamy composition can also act as a moisturizer.

Prolonged controlled release has been achieved using several different devices. Examples include mini-implantable pumps for a variety of drugs especially chemotherapeutics and highly potent neuroactive drugs, silicon tubing with release controlling pores in the ends for birth control agents, and co-axial implants. Currently approved infusion procedures generally use an externally-worn or implanted pump. For example, DUROS™, sufentanil, an osmotic pump designed for 100-day delivery of sufentanil, is currently undergoing clinical testing. This implant is much smaller and easier to administer, and is described in WO 00/54745.

III. Methods of Treatment

A. Local Sustained Release of VEGF

The therapeutic agents, including VEGF protein or recombinant expression systems that provide sustained release of VEGF, may be administered in a single dose, in multiple doses, in a continuous or intermittent manner, depending, for example, upon the recipient's physiological condition. Administration of the compositions may be essentially continuous over an indeterminate period of time, for example, at regular intervals. Alternatively, the compositions can be administered continuously for a pre-selected period of time or in a series of spaced doses.

VEGF can be applied in the form of a gene construct that can produce the gene product in vivo. In one embodiment, an adenovirus delivery system is used to deliver VEGF in a sustained release fashion in vivo. An adenovirus-VEGF (ADV/VEGF) expression system has been shown in experimental models of aging and diabetes and results indicate that this expression system can be an effective in the repair and regeneration of skin. Other means of obtaining sustained release of an effective amount of compound include providing sustained release formulations such as polymeric delivery systems, mini-pumps, and hydrogels, as described above. These can be loaded with VEGF, injected or implanted into the ulcers, where the VEGF is released over a therapeutically effective time period.

In one embodiment, VEGF is delivered as an injectable and administered in combination with dermal abrasion. In this embodiment a single dosing is effective; in other cases, the VEGF must be administered two or more times. In another embodiment, VEGF is applied as cream or other topical formulation as described above, preferably providing sustained release over a period of up to two weeks. Administration can be repeated, for example, once a month, as needed.

B. Effective Dosages

In general, for optimal effects, substantially steady rates of VEGF are delivered to the site of application. Desirable levels of VEGF are those that do not cause adverse side effects. Such an effective dosage can be determined by extrapolation based on animal studies, for example, using a mouse model.

VEGF stimulates simultaneously four cell types: keratinocytes, fibroblasts macrophages and adipocytes. VEGF effects on all these cell types can reverse existing aging effects and prevent new damaging effects. Therefore, the VEGF is administered to provide an effective amount to:

1) promote keratinocyte migration, which can induce smooth appearance of epidermis. For example, in dermal abrasion (removal or scrubbing off the epidermal layer) or any method of exfoliation it stimulates keratinocytes to cover the damaged areas.

2) Promote fibroblast proliferation, since the more fibroblasts, the more collagen. Thinning of skin is one of the aging signs that lead to wrinkling and sagging. More fibroblasts and more collagen reverses this effect.

3) Promote collagen production by the increased number of fibroblasts. More collagen means thicker dermis, thicker skin protects from UV (prevention) and also reverses existing effects. More collagen means stronger skin, reducing wrinkles and preventing those that are generated by grimacing of the face (such as smiling).

4) Promote proper alignment of collagen that is produced so that it is in an orientation in which it is most stable and less susceptible to degradation.

5) Stimulate infiltration of macrophages. These cells provide number of important factors that can also revive (stimulate) fibroblast and keratinocytes to become more active.

The dose range of viral particles is between $10^{11}$ and $10^7$ viral particles. The recombinant protein is delivered in a dosage range of be 10-100 micrograms per square centimeter. The C57BL/KsJ db/db mouse is a particularly useful model since it has been shown to be a clinically relevant model of impaired wound healing. The animals exhibit several characteristics of adult onset diabetes, including obesity, insulin-resistant hyperglycemia and markedly delayed wound closure. C57BL/KsJ-db/db mice, homozygous for the diabetes spontaneous mutation, become identifiably obese around 3 to 4 weeks of age. Elevations of plasma insulin begin at 10 to 14 days and of blood sugar at 4 to 8 weeks. Homozygous mutant mice are polyphagic, polydipsic, and polyuric. The course of the disease is markedly influenced by genetic background. A number of features are observed on the C57BLIKsJ db/db background, including an uncontrolled rise in blood sugar, severe depletion of the insulin-producing beta-cells of the pancreatic islets, and death by 10 months of age. Exogenous insulin fails to control blood glucose levels and gluconeogenic enzyme activity increases. The diabetic mutation is a result of a point mutation in the leptin receptor gene, lepr. This point mutation promotes abnormal splicing creating a stop codon that shortens the intracellular domain of the receptor, so that its signaling capacity is curtailed. The ligand, Leptin, has been shown to be a key weight control hormone that takes a mutant form in the mouse obesity mutation, Lepob (JAX Mice database: http://jaxmice.jax.org/jaxmic-e-cgi/jaxm-icedb.cgi). C57BL/KsJ-db/dbmice exhibit characteristics similar to those of human adult onset diabetes (NIDDM Type 11) as a result of a single autosomal recessive mutation on chromosome 4. Only the homozygous animals develop diabetes. This strain also expresses lower levels of several growth factors and receptors, accounting, at least in part, for the reduced rate of healing (Werner, et al., *J Invest Dermatol,* 103:469-473 (1994)).

The streptozotocin diabetic mouse is another model for studying the pathology of diabetes. Mice are rendered diabetic by intraperitoneal injection of streptozotocin administered for five consecutive days. Streptozotocin-treated mice become hyperglycemic and also show impaired wound healing when compared to healthy animals (Matsuda, et al. *J Exp Med,* 187:297-306 (1998); Brown, et al., *Am J Pathol,* 151: 715-724 (1997)). The streptozotocin-induced diabetic mouse has been widely studied and is known to those of skill in the art.

The diabetic mouse model (Geerlings, et al., *FEMS Immunol Med Microbial.,* 3-4:259-265 (1999); Feige, et al., *EXS.,* 77:359-373 (1996); Bessman, *J Diabetes Complications,* 4:258-262 (1992); Loots, et al., *J Invest Dermatol.,* 5:850-857 (1998); Brown, et al., *J Surg Research,* 56:562-570 (1994); Greenhalgh, et al., *Am J Pathol,* 136:1235-1246 (1990); Tsuboi, et al., *J Explorer Med,* 172:245-251 (1990); Matuxzewska, et al., *Pharm Res,* 11:65-71 (1994); Darby, et al., *Int J Biochem Cell Biol,* 29:191-200 (1997); Livant, et al., *J Clin Invest.,* 105:1537-1545 (2000); Yamamota, et al., *Europ J Pharm,* 302:53-60 (1996); Wetzler, et al., *J Invest Dermatol.,* 115:245-253 (2000); Sun, et al., *J Invest Dermatol,* 108:313-318 (1997); Sun, et al., *J Invest Dermatol.,* 106:232-237 (1996); Zykova, et al., *Diabetes,* 49:1461-1458 (2002); Beer, et al., *Invest Dermatol.,* 109: 132-138 (1997)) has been widely accepted in the study of therapeutic agents that may be effective in the treatment of chronic wounds, it has been successfully used in preclinical testing for other growth factor therapies, and it offers a good model for patients with diabetic foot ulcers.

The present invention will be further understood by reference to the following non-limiting examples.

EXAMPLE 1

Non-Angiogenic Mechanism of VEGF Stimulation of Keratinocyte and Fibroblast Migration Human Recombinant VEGF Stimulates Only the Epidermal Cells (Keratinocytes) that have Regenerative Potential To test the effects of VEGF on epithelialization, which is very important in cosmetology especially for laser resurfacing, recombinant VEGF was tested using an in vitro scratch model to measure keratinocyte migration. When normal human keratinocytes grown in a tissue culture dish are "wounded" by a scratch, they migrate over the scratch to close the gap. This approach was used to test how VEGF effects keratinocyte migration and proliferation.

Materials and Methods

Primary human keratinocytes were incubated in the presence and absence of recombinant VEGF. Keratinocyte migration was observed during a 48 hr period. Epidermal Growth Factor (EGF) was used as a positive control because it is a well established stimulant of both keratinocyte migration and proliferation. Cells were pre-treated with mitomycin C (10 g/ml) for one hour to eliminate effects of proliferation and placed in basal medium (with no growth factors or hormones), scratched, and then immediately photographed. All scratches were photographed at time zero and re-photographed in the same field 24 and 48 hrs later. Similar studies (discussed below) were conducted to determine if VEGF stimulates fibroblasts using primary human dermal fibroblasts and the scratch assay.

Keratinocytes grown in culture medium containing low calcium resemble the activated keratinocytes, the cells that actively participate in tissue repair and regeneration. However, keratinocytes grown in a high calcium medium change their phenotype and become differentiated. As their proliferation rate decreases, they form desmosomal junctions and start stratifying in culture. Once committed to differentiation they progressively lose the regenerative potential, i.e. differentiating cells stop dividing.

When VEGF was tested using differentiated keratinocytes (i.e. those grown in high calcium conditions), it was found that VEGF did not stimulate migration or proliferation in scratch assay experiments. These clinically relevant findings establish that VEGF promotes epithelialization and specifically targets those keratinocytes that have capacity for regeneration. In addition to contributing to the smooth appearance of the skin it may also be used for rapid resurfacing after laser treatments.

Vascular endothelial growth factor (VEGF) is one of the most vital and potent angiogenesis-stimulating growth factors. In this study, the effects of local VEGF on migration of keratinocytes and fibroblasts over wound sites was evaluated using in vitro wound scratch assays. To accomplish this, the migration rates of primary human keratinocytes of two different phenotypes: activated (wound healing) and differentiating in the presence of absence of VEGF, were measured and compared. VEGF was found to accelerate migration of activated keratinocyte. The magnitude of this effect was comparable to EGF. Moreover, this effect was only significant with activated keratinocytes but not with differentiating keratinocytes. This is significant because the keratinocytes normally found at wound sites are activated rather than differentiated.

VEGF Stimulates Migration of Fibroblasts

To determine if VEGF stimulates fibroblasts we perform similar experiments (see above) using primary human dermal fibroblasts and scratch assay. We found that VEGF stimulates migration of fibroblasts. This effect is visible after 8 hrs and scratches were completely closed within 24 hours, indicating rapid response. As expected, EGF (used as a negative control, as a growth factor to which fibroblasts do not respond) did not have an effect on any of the cultures.

These results demonstrate a non-angiogenic effect of VEGF on the wound healing process which emphasizes its potential use in patient with non-healing wounds.

VEGF Stimulates Cells from Elderly Individuals

Effects of VEGF were tested in a scratch assay on primary human fibroblasts deriving from elderly individual. Cells were stimulated with recombinant human $VEGF_{165}$. We found that VEGF stimulates migration of fibroblasts from elderly individuals.

VEGF Effects are Very Fast

The VEGF effects on keratinocytes and fibroblasts (both human and mouse) that we observed were determined either within first 24 hrs (human cells) or three weeks, suggesting very quick biological response. Most clinical studies have stretched it to six months before there are noticeable benefits of retinoids whereas Botox acts within two weeks. Thus VEGF action is not only broader as it encompass beneficial cosmetic effects of both retinoids and botox, but it also has very fast effect.

EXAMPLE 2

VEGF Enhances Skin Healing in Experimental Models as Measured by Tensile Properties of the Skin and Increased Epithelialization Materials and Methods Using methods and materials as described above with respect to VEGF local sustained release of VEGF using adenoviral vector mediated gene transfer reversed the reduced angiogenic response observed in diabetic wounds and accelerated wound healing. This was tested by determining the specific effects of $VEGF_{165}$ application on all components of the wound healing process: epithelialization, skin biomechanical properties, histology, and time to 100% wound closure. To determine the effects of VEGF on wound healing in vivo, $ADV/VEGF_{165}$ and controls (vehicle and saline) were injected into excisional and incisional wounds created on dorsum of BKS.Cg-m+/+$Lepr^{db}$ and NOD mice and mechanical properties and histological evaluations were performed 10, 14 or 21 days post injury.

Linear incisional wounds were created on the dorsum of 57 female BKS.Cg-m+/+$Lepr^{db}$ type 2 diabetic mice. Prior to wounding, the animals were acclimatized for 2 weeks by being placed in individual cages. They were shaved at least one day prior to wounding, and then anesthetized with a mixture of ketamine and xylazine prior to the wounding. A 30-mm linear incision was initiated 5 mm below the last cervical vertebra on the dorsum of each animal in a longitudinal direction. Intradermal injections were administered at both sides of the incision at the 3rd suture location only.

The BKS.Cg-m+/+$Lepr^{db}$ mice were divided into 4 groups based on administered treatment: group I (n=12), ADV/VEGF165 $5 \times 10^{10}$ vp/wound; group II (n=15) ADV/VEGF 165 $5 \times 10^8$ vp/wound, group III (n=15), DL-312 vehicle (positive control) $5 \times 10^8$ vp/wound and group IV (n=15), saline (negative control).

The BKS.Cg-m+/+$Lepr^{db}$ mice were sacrificed at days 10 and 21 post injury for mechanical property analyses of healed wounds. This was accomplished by excising skin containing the incision and performing tensile strength analysis on it.

Skin samples were collected 21 days after VEGF treatment and histological analyses were performed to test if VEGF stimulates collagen production.

Results

Effect on Time to Wound Closure

Wounds treated with ADV/VEGF165, healed 6.6 days faster than controls. Treated wounds healed in 27.25±1.4 days. Saline treated wounds healed in 34.2±7.0 days, while wounds administered with vehicle control alone healed in 33.5±6.5 days. Additionally, analysis of stiffness (N/mm) indicated that skin excised from wound sites of animals treated with $VEGF_{165}$ had a stronger wound breaking strength than skin excised from control animals' wound sites. Furthermore, histological analysis revealed accelerated epithelialization at wound sites treated with $VEGF_{165}$ as measured by analysis of the thickness of the epithelial layer. These results demonstrate that VEGF accelerates closure of wounds and provide evidence for a new mechanism to increase epithelialization at wound sites, through increased migration of keratinocytes.

Effect on Tensile Strength

The BKS.Cg-m+/+$Lepr^{db}$ mice were sacrificed at days 10 and 21 post injury for mechanical property analyses of healed wounds. This was accomplished by excising skin containing the incision and performing tensile strength analysis on it.

Results demonstrated that on Day 21, ADV/VEGF (5×1010) produced statistically significant (p=0.005) increase in tensile stiffness in comparison to vehicle controls (Table 5 below), Day 21 mechanical testing results: BKS.Cgm+/+$Lepr^{db}$ Type 2 diabetic mice). We concluded that VEGF increases tissue strength. By increasing tissue strength it may prevent and/or reduce the wrinkles.

TABLE 4

Effect of different concentrations of $VEGF_{165}$ on tensile strength and stiffness in db/db mice.

| | Group (Vol: 200 ul) | Testing Day | Age (wks) | Pre-wounding BW (g) +/− SD | Pre-testing BW (g) +/− SD | Mice (N) | Stiffness (N/mm) +/− SD | Max Load (N) |
|---|---|---|---|---|---|---|---|---|
| I | ADV/$VEGF_{165}$ ($5 \times 10^{10}$vp) | 10 | 9 | 30 ± 1.7 | 30.1 ± 2.8 | 6 | 0.50 ± 0.2 | 0.83 ± 0.4 |
| II | ADV/$VEGF_{165}$ ($5 \times 10^{8}$vp) | 10 | 9 | 30.8 ± 2.2 | 31.5 ± 3.1 | 6 | 0.59 ± 0.2 | 1.06 ± 0.4 |
| III | Saline (Control) | 10 | 9 | 30.6 ± 4.1 | 34.1 ± 4.7 | 6 | 0.42 ± 0.1 | 0.78 ± 0.2 |
| IV | DL-312 ($5 \times 10^{8}$vp) (Vehicle Control) | 10 | 9 | 31.5 ± 3 | 33.2 ± 3.5 | 6 | 0.32 ± 0.2 | 0.54 ± 0.3 |
| I | ADV/$VEGF_{165}$ ($5 \times 10^{10}$vp) | 21 | 11 | 30 ± 1.8 | 32.9 ± 2.5 | 6 | 1.70 ± 0.2 | 4.27 ± 0.7 |
| II | ADV/$VEGF_{165}$ ($5 \times 10^{8}$vp) | 21 | 11 | 32 ± 3.0 | 34.1 ± 4.3 | 6 | 1.53 ± 0.4 | 4.46 ± 0.9 |
| III | Saline (Control) | 21 | 11 | 31.2 ± 1.9 | 34.2 ± 4.3 | 6 | 1.17 ± 0.15 | 3.57 ± 0.6 |
| IV | DL-312 ($5 \times 10^{8}$vp) (Vehicle Control) | 21 | 11 | 31.1 ± 2.3 | 33.2 ± 1.6 | 6 | 1.13 ± 0.2 | 3.72 ± 0.6 |

VEGF Induced Fibroblasts Proliferation and Promotes Collagen Deposition

To test if VEGF stimulates collagen production skin samples were collected after VEGF treatment and histological analyses were performed. The volume of granulation tissue was more rapidly reduced in the ADV/hVEGF treated open wounds compared to the other two treatment groups. The cellular density of ADV/hVEGF treated wounds compared to saline and empty virus treated wounds were clearly shown histologically. Saline control wounds contained granulation tissue with a modest cell density and few blood vessels). Most of the cell populations in these saline treated wounds were mesenchymal cells. The empty virus particle treated mouse wounds, like the saline controls, had a modest cell density with few obvious blood vessels present. The ADV/hVEGF treated wounds were showed prominent changes in granulation tissue. Granulation tissue within the ADV/hVEGF treated wounds was thicker in depth and was made up of a greater cell density compared to the saline and empty viral particle controls). The density and luminal size of the blood vessels in the ADV/hVEGF treated wounds was greater than the other groups, suggesting induced angiogenesis. By histological evaluation ADV/hVEGF treated wounds showed enhanced granulation tissue deposition containing more cells and blood vessels compared to the non-VEGF treated wounds. This means that VEGF treated skin shows increase in number of fibroblasts (induction of proliferation) and thicker granulation tissue (Increase in collagen deposition) that untreated skin.

The VEGF effects on keratinocytes and fibroblasts (both human and mouse) that were observed were determined either within the first 24 hrs (human cells) or three weeks, indicating a very quick biological response. Most clinical studies using retinoids require six months before there are noticeable benefits. Thus the VEGF effect is not only broader as it encompass beneficial cosmetic effects of both retinoids and botox, but it is also very quick.

Various retinoids were shown to increase collagen synthesis and concentration in the skin and reduce their rate of degradation. [Sorg, et al: Proposed mechanisms of action for retinoid derivatives in the treatment of skin aging. *J Comet Dermatol.*, 4(4):237-44 (2005).] Retinoids penetrate deep into skin where they stimulate cell division. This has two effects: repairing the top layer of skin and enhancing the production of collagen. We demonstrate that VEGF stimulates fibroblast cell division and production of collagen. Tretinoin is often prescribed before laser resurfacing in an attempt to enhance results. Orringer et al found no evidence of enhanced collagen formation, accelerated re-epithelialization, or quicker resolution of postoperative erythema with tretinoin pretreatment before laser resurfacing. [Orringer, et al., *J Am Acad Dermatol.*, 51(6):940-6 (2004). Tretinoin treatment before carbon-dioxide laser resurfacing: a clinical and biochemical analysis]. We demonstrate here that VEGF would be an ideal agent that enhances collagen and accelerates regeneration in epithelium.

VEGF Increases Epithelial Thickness and Smooth Appearance

To determine the effects of VEGF on the epidermis, histological analyses of the treatment groups described above was analyzed with respect to the epidermal layer.

It was found that the epidermal layer over ADV/hVEGF treated wounds was thicker. Thickness of epidermal layer was observed on histology sections. It was evident that ADV-VEGF treated samples have increase in keratinocyte (epidermal) cell layers when compared to saline or ADV controls. This indicates that VEGF stimulates keratinocyte proliferation, which in turn results in more cellular epidermis that gives skin the smooth appearance.

Summary

VEGF has powerful anti-aging effects on skin. VEGF induces fibroblast proliferation and migration, collagen production and proper alignment, increases tissue strength, promotes epidermal migration and proliferation, increasing the smoothness of the skin. This means that if applied topically or locally injected it will have a profound anti-aging effect that will not only reduce the appearance of wrinkles but prevent their new formation simultaneously.

EXAMPLE 7

VEGF Induces Collagen Formation with Alignment of Fibers

One of the contributing factors to wrinkle formation is loss of alignment in collagen fibers. To test if the VEGF-mediated collagen deposition is properly aligned, Sirius red staining with polarized light microscopy was employed on the three treatment groups of Example 6.

Saline treated control wounds showed modest birefringence intensity from organized collagen fibers. These collagen fibers were short, thin and arranged in a random pattern. The greenish-yellow birefringence of these collagen fibers was typical of young immature granulation tissue. The red birefringence on the surface of the granulation tissue was from the keratin laid-down by keratinocytes within the epidermal cell layer. There was little collagen deposited in these saline treated mice and that newly deposited collagen was poorly organized. Empty viral particles treated wounds show an increase in the greenish-yellow birefringence intensity, where collagen fibers were arranged in a more parallel fashion compared to saline treated controls. The increase in collagen deposition and organization might have been from viral particles, causing an inflammatory response early in the repair process, which occurred soon after viral treatment that promoted a modest increase in connective tissue deposition. The Sirius red stained polarized light viewed ADV/hVEGF treated wounds showed an intense reddish-yellow birefringence pattern, where collagen fibers were long, thick and had a strong association with one another. The intense reddish-yellow color was in contrast to the greenish-yellow birefringence color of the saline and empty viral particle treated wounds. The reddish-yellow intense birefringence was consistent with a greater amount of collagen deposited, which was laid down in a more organized fashion.

In conclusion, VEGF not only induces collagen deposition but it also promotes its proper alignment, which may prevent formation of wrinkles and reduce appearance of existing ones.

EXAMPLE 8

VEGF Induces Tissue Formation, not Just Blood Vessel Ingrowth

The PVA (poly-vinyl alcohol) sponge model emulates a wound. This model is useful, in conjunction with other models, to minimize variables in independently quantifying growth factor release and specifying histological parameters. VEGF clearly accelerates healing in sponge models.

Materials and Methods

Wounding The animals were shaved on their back with an electric shaver (Oster 76®, 0.05 mm detachable blade, USA) under anesthetization with Ketamine (50 mg/kg) and Xylazine (5 mg/kg). Briefly, 1 ml 100 mg/ml Ketamine (Fort Dodge, Iowa, USA), 0.5 ml 20 mg/kg xylazine (Bayer Corporation, Shawnee, Mission, Kans., USA) and 4.7 ml nounal saline were mixed well. 0.1 ml well mixed solution was injected intraperitoneal per 30 g mouse. PVA sponges were moistened, sterilized by boiling, patted dry, then injected with 250 µl of the growth factor. Over the mid-dorsum of the mouse, 12.7 mm×3 mm non-sterile PVA (Polyvinyl Alcohol) Sponge (M-PACT, Eudora, Kans., USA) was implanted subcutaneously 15 mm below the skull base.

Fourteen (14) days after PVA Sponge implantation, the animals were sacrificed by carbon dioxide asphyxiation and the sponges were harvested by excising the area surrounding the sponge. The sponge wass washed with PBS, and then cut into 2 sections, in which one is immediately placed into a −80° C. freezer and the other half fixed in 10% neutral buffered formalin. The sponge was then embedded in paraffin, sectioned 4-5 microns thick, and stained with H&E for vessel density and CD-31 (Pecam) for histological analysis to visualize the endothelium.

Results

PVA wound sponges from diabetic mice, treated with VEGF $5\times10^8$ vp/wound and DL-312 $5\times10^8$ (viral vector control) vp/wound and stained with CD31 (for angiogenesis), were examined by histology. The density, size and morphology of blood vessels within granulation tissue defined how the angiogenic process affects/correlates with other factors contributing to the healing response in mice. The results clearly demonstrate that the VEGF is responsible not just for blood vessel ingrowth but migration into the wound of fibroblasts and other materials forming collagen.

Conclusions

Epidermal Effects of VEGF

VEGF selectively stimulates keratinocytes with regenerative potential. VEGF increases epidermal thickness. This contributes to smooth appearance (anti-wrinkle) effect. VEGF increases epidermal thickness by increasing number of cellular layers in epidermis. This serves as protection from UV-photo damage, thus it acts as anti-aging agent.

Dermal Effects of VEGF

VEGF stimulates fibroblast migration and proliferation. This contributes to anti-wrinkle effect. VEGF increases dermal thickness. This contributes to smooth appearance of the skin and reduction of wrinkles. VEGF stimulates collagen deposition. This has dual effect: it reduces wrinkles and functions as a filler. VEGF increases tensile strength of the skin. This contributes to reduction of wrinkles and increases elasticity. VEGF stimulates fibroblasts from elderly (anti-aging effect). VEGF can also be administered to the skin following dermal abrasion, for treating conditions wherein collagen stimulation, epidermal stimulation or fat deposition would be beneficial, or for enhancing epidermal. Further application of VEGF include but are not limited to lip augmentation, wrinkle reduction, enhancement of facial fullness, fill deep creases, build up contours, dermal abrasion, reconstructive surgery, any condition where UV radiation is needed, treatment with skin grafts, radiation injury, tobacco injury to skin, and after chemotherapy or anticancer therapy.

We claim:

1. A method of increasing collagen formation in intact skin comprising administering topically or locally to intact skin a composition wherein the active ingredient consists of Vascular Endothelial Growth Factor (VEGF) in an effective amount to increase collagen formation in the intact skin.

2. The method of claim 1 comprising administering the composition to the surface of the skin to be treated, wherein the active agent in the composition consists of VEGF in a formulation for topical application to the skin.

3. The method of claim 1 comprising administering the composition by intradermal or subcutaneous injection, wherein the active agent in the composition consists of VEGF in a pharmaceutically acceptable carrier for injection.

4. The method of claim 1, wherein the composition comprises a sustained or controlled release formulation providing VEGF at the site to be treated for between one and 10 days.

5. The method of claim 1 further comprising exfoliation prior to or at the time of administration of the VEGF.

6. The method of claim 1, wherein the collagen formation comprises collagen deposition.

7. The method of claim 1, wherein the composition is administered to the intact skin of a subject with wrinkled skin.

8. The method of claim 1, wherein the VEGF is administered to the skin in combination with an exfoliant or laser treatment.

9. The method of claim 1, wherein the VEGF is administered to the intact skin following or at the time of surgical removal or reshaping of the skin.

10. The method of claim 1, wherein the composition is administered to fine lines, wrinkles, age spots, or a combination thereof.

11. The method of claim 1, wherein the composition is administered to skin damaged by disease or sun.

12. The method of claim 1, wherein the composition is administered to the intact skin of a subject with diabetes.

13. A method of increasing migration of activated keratinocytes in intact skin comprising administering topically or locally to intact skin a composition wherein the active ingredient consists of Vascular Endothelial Growth Factor (VEGF) in an effective amount to increase migration of the activated keratinocytes in the intact skin.

14. The method of claim 13 comprising administering the composition to the surface of the skin to be treated, wherein the active agent in the composition consists of VEGF in a formulation for topical application to the skin.

15. The method of claim 13 comprising administering the composition by intradermal or subcutaneous injection, wherein the active agent in the composition consists of VEGF in a pharmaceutically acceptable carrier for injection.

16. The method of claim 13, wherein the composition comprises a sustained or controlled release formulation providing VEGF at the site to be treated for between one and 10 days.

17. The method of claim 13, further comprising exfoliation prior to or at the time of administration of the VEGF.

18. The method of claim 13, wherein the composition is administered to the skin of a subject with wrinkled skin.

19. The method of claim 13, wherein the VEGF is administered to the skin in combination with an exfoliant or laser treatment.

20. The method of claim 13, wherein the VEGF is administered to the intact skin following or at the time of surgical removal or reshaping of the skin.

21. The method of claim 13, wherein the composition is administered to fine lines, wrinkles, age spots, or a combination thereof.

22. The method of claim 13, wherein the composition is administered to skin damaged by disease or sun.

23. The method of claim 13, wherein the composition is administered to the intact skin of a subject with diabetes.

* * * * *